(12) United States Patent
Myung et al.

(10) Patent No.: US 10,610,088 B2
(45) Date of Patent: Apr. 7, 2020

(54) MULTI-WAVELENGTH ENDOSCOPIC SYSTEM AND IMAGE PROCESSING METHOD USING SAME

(71) Applicant: THE ASAN FOUNDATION, Seoul (KR)

(72) Inventors: Seung-Jae Myung, Seoul (KR); Sang-Yeob Kim, Seoul (KR); Sang Mun Bae, Seoul (KR); Eun-Ju Do, Seoul (KR); Dong-Jun Bae, Gyeonggi-do (KR)

(73) Assignee: THE ASAN FOUNDATION, Seoul (KR)

( * ) Notice: Subject to any disclaimer, the term of this patent is extended or adjusted under 35 U.S.C. 154(b) by 0 days.

(21) Appl. No.: 16/342,900

(22) PCT Filed: Oct. 18, 2017

(86) PCT No.: PCT/KR2017/011522
§ 371 (c)(1),
(2) Date: Apr. 17, 2019

(87) PCT Pub. No.: WO2018/074833
PCT Pub. Date: Apr. 26, 2018

(65) Prior Publication Data
US 2019/0239730 A1    Aug. 8, 2019

(30) Foreign Application Priority Data
Oct. 18, 2016    (KR) .................. 10-2016-0135305

(51) Int. Cl.
*A61B 1/04*    (2006.01)
*A61B 1/06*    (2006.01)
(Continued)

(52) U.S. Cl.
CPC ............... *A61B 1/043* (2013.01); *A61B 1/05* (2013.01); *A61B 1/0661* (2013.01); *A61B 1/31* (2013.01);
(Continued)

(58) Field of Classification Search
CPC ....... A61B 1/042; A61B 1/00186; A61B 1/05; A61B 1/0661; A61B 1/00009; A61B 1/31;
(Continued)

(56) References Cited

U.S. PATENT DOCUMENTS 7,139,598 B2    11/2006  Hull et al.
8,214,025 B2     7/2012  Takaoka et al.
(Continued)

FOREIGN PATENT DOCUMENTS

JP    2003-339623    12/2003
JP         4954699     6/2012
(Continued)

OTHER PUBLICATIONS

International Searching Authority, International Search Report, issued in connection with International Patent Application No. PCT/KR2017/011522 dated Jan. 12, 2018, 11 pages.
(Continued)

*Primary Examiner* — Bo Joseph Peng
(74) *Attorney, Agent, or Firm* — Hanley, Flight & Zimmerman, LLC

(57) ABSTRACT

There is disclosed a multi-wavelength endoscopic system for imaging an observation site labeled with a plurality of fluorescent materials having different colors. The system includes an imaging unit configured to acquire image data by polarizing incident light reflected from the observation site in a first direction and a second direction perpendicular to the first direction, dividing a spectrum region of the
(Continued)

incident light polarized in the first direction and the second direction into a plurality of spectrum channels and measuring the intensity of light for each of the spectrum channel. The system further includes a computing unit configured to store a single fluorescence spectrum extracted from sample image data obtained by single-treating the observation site with each of the fluorescent materials and configured to separate and output the image data obtained in the imaging unit using the single fluorescence spectrum so that each of the fluorescent materials is displayed separately.

7 Claims, 10 Drawing Sheets

(51) Int. Cl.
*G01N 21/64* (2006.01)
*A61B 1/05* (2006.01)
*A61B 1/31* (2006.01)

(52) U.S. Cl.
CPC ......... *G01N 21/64* (2013.01); *G01N 21/6456* (2013.01); *G01N 2021/6421* (2013.01)

(58) Field of Classification Search
CPC ..... A61B 1/0638; A61B 1/043; A61B 5/0084; A61B 5/0071; G06T 7/0012; H02P 23/14; G01N 21/64; G01N 21/6456; G01N 2021/6421

See application file for complete search history.

(56) References Cited

U.S. PATENT DOCUMENTS

2003/0078477 A1  8/2003  Kang et al.
2003/0218137 A1  11/2003  Sendai

FOREIGN PATENT DOCUMENTS

| JP | 5506472 | 5/2014 |
| KR | 10-0411631 | 12/2003 |
| KR | 10-2007-0054761 | 5/2007 |
| KR | 10-1243183 | 3/2013 |
| KR | 10-2016-0117440 | 10/2016 |
| WO | 2015/103420 | 7/2015 |

OTHER PUBLICATIONS

Korean Patent Office, Office Action, issued in connection with Korean Patent Application No. 10-2016-0135305, dated Nov. 11, 2018, 7 pages.

Korean Intellectual Property Office, "Notice of Preliminary Rejection," dated Nov. 13, 2018 in connection with Korean Patent Application No. 10-2016-0135305, 13 pages. Full document and English translation attached.

Korean Intellectual Property Office, "Notice of Preliminary Rejection," dated Mar. 6, 2019 in connection with Korean Patent Application No. 10-2016-0135305, 4 pages. Full document and English translation attached.

Korean Intellectual Property Office, "Notice of Allowance," dated Apr. 30, 2019 in connection with Korean Patent Application No. 10-2016-0135305, 4 pages. Full document and English translation attached.

Korean Intellectual Property Office, "Notice of Allowance," dated Apr. 30, 2019 in connection with Korean Patent Application No. 10-2016-0135305 (4 pages).

MULTI-WAVELENGTH ENDOSCOPIC SYSTEM AND IMAGE PROCESSING METHOD USING SAME

TECHNICAL FIELD

The present invention relates to a multi-wavelength endoscopic system and an image processing method using same.

BACKGROUND

Cancer incidents still occur at a high rate. When cancer is diagnosed through endoscopy, there is a possibility of misdiagnosis because the tumor must be detected by the naked eye.

Particularly, if a polyp has a flat shape rather than a lump shape, the probability for detecting the polyp is further lowered.

In recent years, along with the development of molecular imaging technology, there have been ongoing studies to diagnose gastrointestinal cancer and to image the molecular characteristics of cancer using this technology. The first attempt was to introduce the possibility of applying molecular imaging that targets Cathepsin B to endoscopy. However, the images at that time were too simple to be applied at a clinical level.

Related studies have been carried out in various institutions. Until recently, a technique for imaging a specific tumor tissue using a peptide as a probe, an ultra-small imaging technique capable of high-speed three-dimensional endoscopic imaging and a small microscope technique have been developed. A more advanced marker material is being developed through the development of a Raman amplification probe capable of ultra-sensitive molecular imaging and an aptamer-based compact fluorescent probe.

The group of Dr. Goetz of Mainz University in Germany has developed a probe that can identify an Epidermal Growth Factor Receptor (EGFR) and has attempted to image the probe using a special endoscope called a confocal endomicroscope.

Although studies for enabling endoscopy using molecular imaging have been conducted thus far, there has been little study that has obtained images at a level applicable to actual endoscopes. Even in the case of a probe that is very important in molecular imaging, there is available only a technique at a level that can only confirm and verify a probe for a single target.

SUMMARY

Embodiments of the present invention provide a multi-wavelength endoscopic system capable of processing image data obtained by imaging an observation site labeled through the use of multiple probes for a composite target and capable of providing the processed image data to the diagnosis of disease, and an image processing method using same.

In accordance with a first aspect of the present invention, there is provided a multi-wavelength endoscopic system for imaging an observation site labeled with a plurality of fluorescent materials having different colors, including: an imaging unit configured to acquire image data by polarizing incident light reflected from the observation site in a first direction and a second direction perpendicular to the first direction, dividing a spectrum region of the incident light polarized in the first direction and the second direction into a plurality of spectrum channels and measuring an intensity of light for each of the spectrum channels; and a computing unit configured to store a single fluorescence spectrum extracted from sample image data obtained by single-treating the observation site with each of the fluorescent materials and configured to separate and output the image data obtained in the imaging unit using the single fluorescence spectrum so that each of the fluorescent materials is displayed separately.

The imaging unit may include: a beam splitter configured to polarize the incident light in the first direction and the second direction perpendicular to the first direction; a first area filter positioned in a path of a light beam split in the first direction and configured to pass a light beam falling within a predetermined spectral range; a second area filter positioned in a path of a light beam split in the second direction and configured to pass a light beam falling within a predetermined spectral range; a first area camera configured to measure an intensity of the light beam passing through the first area filter; and a second area camera configured to measure an intensity of the light beam passing through the second area filter.

The computing unit may be configured to store an untreated fluorescence spectrum extracted from untreated image data obtained by imaging the observation site not labeled with the fluorescent materials.

The computing unit may be configured to perform a correction to remove an auto-fluorescence component contained in the image data obtained in the imaging unit using the untreated fluorescence spectrum.

In accordance with a second aspect of the present application, there is provided a multi-wavelength endoscopic system for imaging an observation site labeled with a plurality of fluorescent materials having different colors, including: a beam splitter configured to polarize incident light reflected from the observation site in a first direction and a second direction perpendicular to the first direction; a first area filter positioned in a path of a light beam split in the first direction and configured to pass a light beam falling within a predetermined spectral range; a second area filter positioned in a path of a light beam split in the second direction and configured to pass a light beam falling within a predetermined spectral range; a first area camera configured to measure an intensity of the light beam passing through the first area filter; a second area camera configured to measure an intensity of the light beam passing through the second area filter; and a computing unit configured to separate and output the image data obtained using the intensity of the light beam passing through the first area filter and the intensity of the light beam passing through the second area filter so that each of the fluorescent materials is displayed separately.

The computing unit may be configured to store a single fluorescence spectrum extracted from sample image data obtained by single-treating the observation site with each of the fluorescent materials and is configured to separate the image data using the single fluorescence spectrum so that each of the fluorescent materials is displayed separately.

The computing unit may be configured to store an untreated fluorescence spectrum extracted from untreated image data obtained by imaging the observation site not labeled with the fluorescent materials.

The computing unit may be configured to perform a correction to remove an auto-fluorescence component contained in the image data using the untreated fluorescence spectrum.

In accordance with a third aspect of the present application, there is provided an image processing method for processing an image using a multi-wavelength endoscopic system, including: irradiating light on an observation site labeled with a plurality of fluorescent materials having different colors; acquiring image data by receiving a light reflected from the observation site; separating the image data so that only one of the fluorescent materials is displayed; and outputting the separated image data according to a wavelength band.

The method may further include extracting a single fluorescence spectrum from sample image data obtained by single-treating the observation site with each of the fluorescent materials.

In separating the image data, the image data may be separated using the single fluorescence spectrum so that each of the fluorescent materials is displayed separately.

The method may further include extracting an untreated fluorescence spectrum from untreated image data obtained by imaging the observation site not labeled with the fluorescent materials.

The method may further include performing a correction to remove an auto-fluorescence component contained in the image data using the untreated fluorescence spectrum.

The multi-wavelength endoscopic system according to the embodiment of the present invention can separate and output an observation region labeled with a plurality of probes according to a predetermined wavelength band. This makes it possible to accurately grasp a disease occurrence region.

The multi-wavelength endoscopic system according to the embodiment of the present invention can output image data by removing an auto-fluorescence component contained in the image data obtained by imaging an observation region. This makes it possible to reduce false positive errors, thereby reducing the possibility of misdiagnosis.

DETAILED DESCRIPTION

Figure 1:
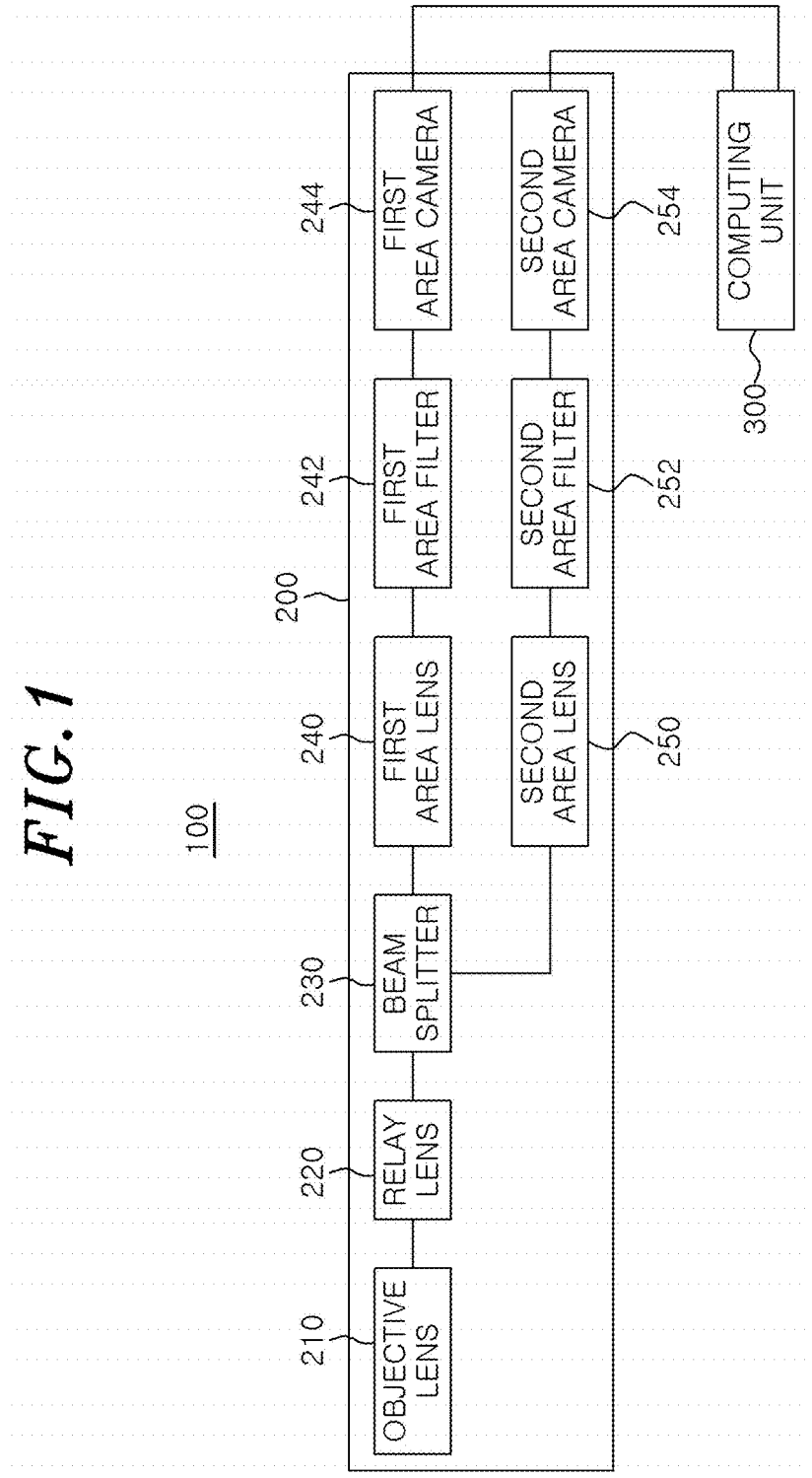
FIG. 1 is a configuration diagram of a multi-wavelength endoscopic system according to an embodiment of the present invention.

Hereinafter, exemplary embodiments of the present invention will be described in detail with reference to the accompanying drawings, which will be readily apparent to those skilled in the art to which the present invention pertains. However, the present invention can be implemented in various different forms, and is not limited to the embodiments described herein. In order to clearly illustrate the present invention, parts not related to the description are omitted, and like parts are denoted by like reference numerals throughout the specification.

Throughout the specification, when some component "includes" some element, it should be understood that the some component can include other elements as well, rather than excluding other elements unless specifically stated otherwise. A term such as "part", "unit", "module" or the like disclosed in the specification indicates a unit for processing at least one function or operation, and may be implemented in hardware, software or in combination of hardware and software.

Hereinafter, a multi-wavelength endoscopic system according to an embodiment of the present invention will be described in detail with reference to the drawings.

Figure 2:
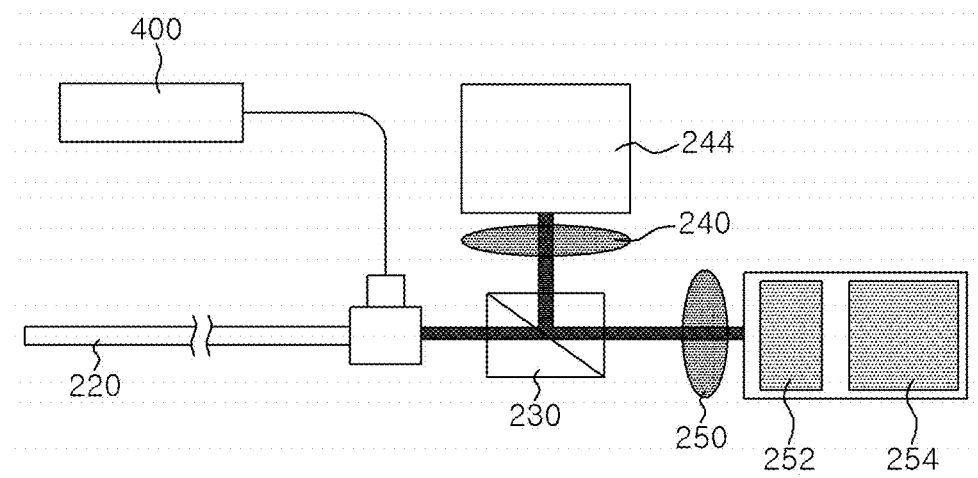
FIG. 2 is a view illustrating a structure of an imaging unit according to an embodiment of the present invention.
Figure 3:
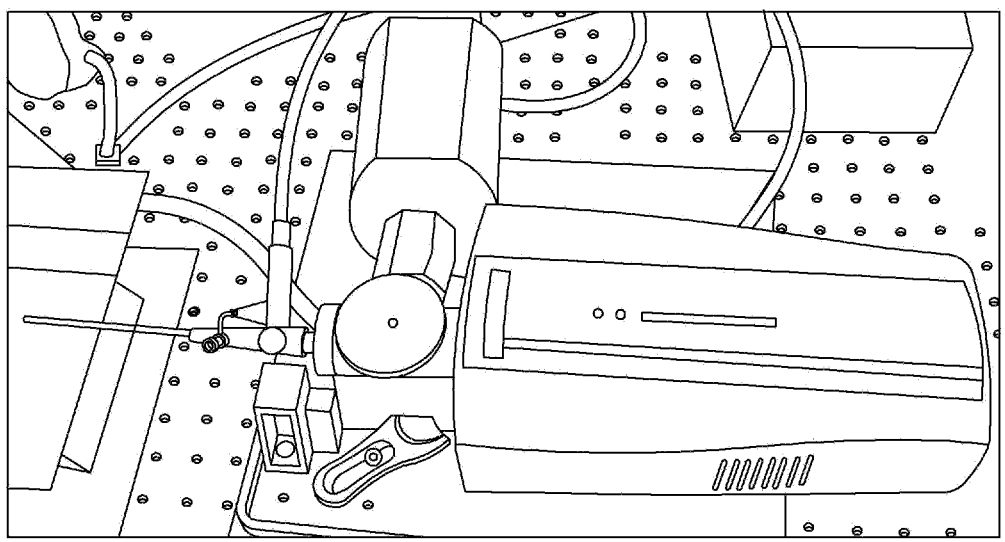
FIG. 3 is a view illustrating an imaging unit according to an embodiment of the present invention.

FIG. 1 is a configuration diagram of a multi-wavelength endoscopic system according to an embodiment of the present invention. FIG. 2 is a view illustrating a structure of an imaging unit according to an embodiment of the present invention. FIG. 3 is a view illustrating an imaging unit according to an embodiment of the present invention.

Referring to FIG. 1, the multi-wavelength endoscopic system 100 is a system using a camera that makes it possible to visually observe an object to be detected and a camera adopting a filter that enables multi-fluorescence imaging. The multi-wavelength endoscopic system continuously images a visible light region to obtain the hyper-spectral radiation luminance of each channel.

In this regard, the channel is a unit band for measuring wavelength. A spectral image of each channel can be obtained by adjusting a filter.

In the subject specification, an endoscope generally refers to an instrument for observing the inside of a human body and includes, e.g., a bronchoscope, a gastroscope, a laparoscope and an anoscope.

The multi-wavelength endoscopic system 100 includes an imaging unit 200 and a computing unit 300.

The imaging unit 200 includes an objective lens 210, a relay lens 220, a beam splitter 230, a first area lens 240, a first area filter 242, a first area camera 244, a second area lens 250, a second area filter 252, and a second area camera 254.

A light source 400 shown in FIG. 2 and located outside the multi-wavelength endoscopic system 100 irradiates light so as to excite a region to be imaged. The light source 400 may include two or more light sources having different wavelengths so as to image an observation target labeled with fluorescent samples having different wavelengths.

In this embodiment, the observation target is a marker expressed in cancer. In this embodiment, the marker may be labeled using probes labeled with different fluorescent material having various wavelength bands.

The objective lens 210 is a lens through which incident light enters. The objective lens 210 may provide an image focused regardless of the wavelength in the spectral region of the multi-wavelength endoscopic system 100.

The relay lens 220 is a lens for advancing incident light along an optical axis and is configured to output light in parallel. The relay lens 220 may be a triplet lens having a predetermined focal length.

Referring to FIG. 2, the relay lens 220 according to the present embodiment may be connected to the light source 400 that emits light for exciting a region to be imaged. The relay lens 220 may be positioned inside the endoscope inserted into the body to image a diagnosis target.

The beam splitter 230 separates the parallel light into two light beams. The beam splitter 230 is a polarization-based beam splitter that processes incident light having a wide-band spectrum. The beam splitter 230 may cover the spectrum falling within a visible light region.

Light consisting of electric fields in various directions is polarized into two light beams called a p-polarized light beam and an s-polarized light beam. In this regard, the p-polarized light beam means a light beam parallel to a slit direction of a polarization plate, and the s-polarized light beam means a light beam perpendicular to the slit direction of the polarization plate.

The first area lens 240 and the second area lens 250 are respectively located in the paths of the light beams split from the beam splitter 230. In order to adjust the light beams split from the beam splitter 230 at a predetermined magnification, the first area lens 240 and the second area lens 250 are disposed perpendicularly to each other so that they can acquire the light beams split from the beam splitter 230.

The first area lens 240 and the second area lens 250 may adjust the light beams split from the beam splitter 230 at an appropriate magnification and may transmit the adjusted light beams to the first area filter 242 and the second area filter 252, respectively.

The first area filter 242 and the second area filter 252 can pass the light beams falling within a specified spectral range among the light beams passed through the first area lens 240 and the second area lens 250, respectively.

The first area filter 242 and the second area filter 252 may be, for example, a liquid crystal tunable filter (LCTF), which is a local band-pass filter for passing a light beam falling within a specified spectral region.

When an LCTF that passes a channel of a specific wavelength band in a spectral region (for example, 440 nm to 720 nm) is used as the filter of the present system, it may be possible to control the filter so as to pass a light beam at, for example, 10 nm intervals.

The LCTF is capable of electronically converting a wavelength and, therefore, selecting a wavelength at a high speed.

Figure 4:
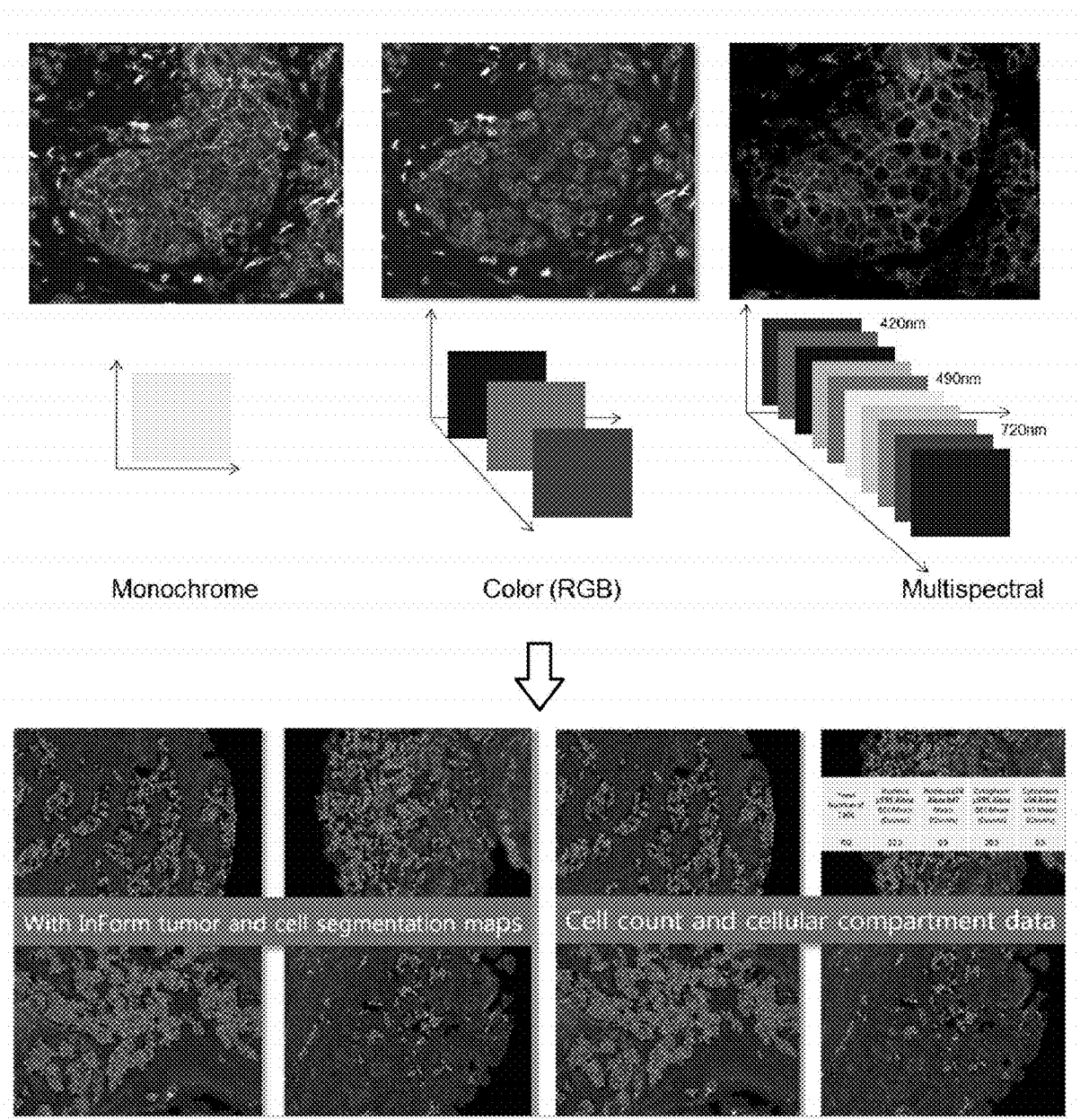
FIG. 4 is a view illustrating a result of driving a variable liquid crystal filter according to an embodiment of the present invention.

Referring to FIG. 4, the LCTF (www.perkinelmer.co.kr) may be controlled to pass light at predetermined intervals and has an effect of putting several tens to several hundreds of filters in one filter. Therefore, it is possible to realize multi-wavelength imaging in vivid and diverse colors.

Referring again to FIG. 1, the first area camera 244 and the second area camera 254 are disposed at the ends of the respective optical paths to measure the intensity of the light beams passing through the first area filter 242 and the second area filter 252.

The first area camera 244 and the second area camera 254 may be monochrome cameras. In this case, the first area camera 244 and the second area camera 254 may acquire the intensity of the image focused through respective positive triplet lenses having predetermined focal distances.

The computing unit 300 may sort the spectral images of the respective channels acquired by the imaging unit 200 and may output the radiance corresponding to the wavelength. The multi-spectral image may be composed of a combination of spectral images imaged from a plurality of channels.

The computing unit 300 may separate and output the multi-spectral images captured by the imaging unit 200 according to the wavelength band.

In this embodiment, in order to accurately diagnose a disease by accurately detecting various disease-related markers at a site to be imaged, the site to be imaged may be labeled with fluorescent materials having different wavelengths.

In the case of labeling a single marker with a single fluorescent material, it is difficult to accurately determine a lesion. Therefore, in this embodiment, a complex probe is labeled with fluorescent materials having different wavelengths, whereby different probes can be supplemented to accurately image a lesion.

The spectral image obtained by imaging the region labeled with fluorescent materials having different wavelengths through the use of the imaging unit 200 may indicate fluorescent signals having different wavelength regions.

When a plurality of markers labeled with fluorescent materials having different wavelengths is used to image an observation site, the fluorescent materials may generate interference in the image. This may make it difficult to distinguish the respective fluorescent materials.

In addition, a material other than the markers labeled with the fluorescent materials in the region to be imaged may be irradiated with the excitation light emitted from the light source 400 so as to emit intrinsic light.

For example, there may be generated an auto-fluorescence phenomenon, in which collagen, elastin, keratin, NADH, flavin, porphyrin or the like contained in the biological tissue to be observed, reflects the excitation light.

There is a possibility of misdiagnosis when diagnosing a disease through the use of an imaging result in which an auto-fluorescent material generally distributed inside the body rather than the marker material to be detected is erroneously regarded as a marker due to the auto-fluorescence phenomenon.

Accordingly, the computing unit 300 of the multi-wavelength endoscopic system according to an embodiment of the present invention is configured to separate and output the imaging result acquired by the imaging unit 200 depending on the wavelength bands of the respective fluorescent materials, so that the user can accurately diagnose a disease using a multi-spectral image as an imaging result.

At this time, the computing unit 300 may extract an auto-fluorescence spectrum result indicating the intensity of the light corresponding to a wavelength band from the auto-fluorescence image obtained by imaging a non-treated tissue sample that is not treated with a fluorescent material in advance.

In addition, the computing unit 300 may extract a single fluorescence spectrum result indicating the intensity of the light corresponding to a wavelength band from a plurality of single treated images obtained by imaging a tissue sample that is single-treated with a fluorescent material.

First, the computing unit 300 extracts an image spectrum result indicating the intensity of the light corresponding to a wavelength band from the image data obtained by the imaging unit 200, and performs a correction of deleting the auto-fluorescence portion by attenuating the image spectrum result by just as much as the intensity of the light corresponding to each wavelength band according to the spectrum of the auto-fluorescence image.

The computing unit 300 may calculate a normalized numerical value indicating the intensity of the light corresponding to a wavelength band from the single fluorescence spectrum. For example, the ratio of intensities of the light corresponding to each wavelength band may be calculated by setting the intensity of the light corresponding to the entire wavelength band to 100.

Next, the computing unit 300 separates (unmixes) the image spectrum result of the image data by the intensity of the light corresponding to each wavelength band according to the normalized numerical value calculated from the single fluorescence spectrum, whereby the image obtained by imaging the observation site labeled with a plurality of fluorescent materials may be separated into a plurality of images so that only the respective fluorescent materials appear.

Accordingly, the computing unit 300 according to an embodiment of the present invention may perform correction to remove the auto-fluorescence component from the multi-spectral image in order to reduce the probability of misdiagnosis when diagnosing a disease according to the imaging result. This makes it possible to display only a marker labeled with a fluorescent material.

In addition, by separating the image of the observation site labeled with a plurality of markers so that only each of the markers is displayed, it is possible to accurately diagnose a cancer lesion by supplementing the different markers.

Figure 5:
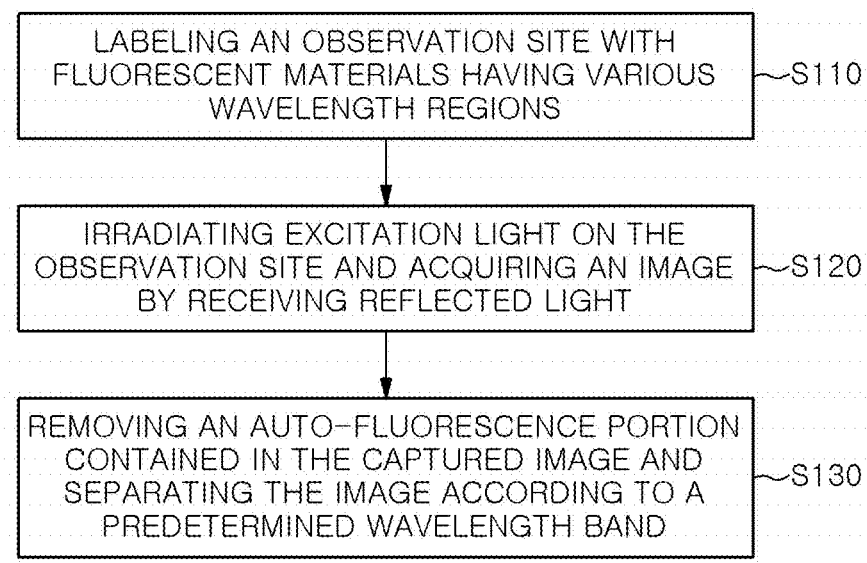
FIG. 5 is a flowchart illustrating an image processing method using the multi-wavelength endoscopic system according to an embodiment of the present invention.

FIG. 5 is a flowchart illustrating an image processing method using the multi-wavelength endoscopic system according to an embodiment of the present invention.

Referring to FIG. 5, the region to be imaged is labeled with a fluorescent material in various wavelength bands (S110). In this experimental example, the region to be imaged may be internal body tissue for cancer screening. A marker expressed in cancer may be labeled using a probe labeled with a fluorescent material in various wavelength bands.

Table 1 shows various area probes for multi-wavelength detection.

| Probe name | Marker | Labeling material | Wavelength band (nm) |
|---|---|---|---|
| HMRG | g-Glutamyl transpeptidase | Rhodamine | 501-524 |
| Cetuximab | EGFR receptor | Flamma-553 | 553-570 |
| Herceptin | Her-2 receptor | Flamma-675 | 675-700 |

The probes may be antibody probes. In this embodiment, the antibody probes may be Cetuximab and Herceptin, which are targeted antibodies to EGFR and HER2, frequently expressed in tumor and colon cancer cells. In this embodiment, Cetuximab and Herceptin are labeled with fluorescent materials Flamma-553 and Flamma-675, respectively.

Furthermore, the probes may be active probes. In this embodiment, the active probe may be gGlu-HMRG, which exhibits fluorescence activity when meeting with GGT (γ-glutamyltranspeptidase), frequently expressed in tumor cells and colon cancer cells. In this embodiment, HMRG may be labeled with Rhodamine.

The antibody probe may be intravenously administered to the tail of a mouse 48 hours prior to acquiring a multi-wavelength detection endoscopic image. The active probe may be applied to the colon 10 minutes prior to performing the multi-wavelength detection endoscopy.

Then, the excitation light is irradiated on the region to be imaged, and a captured image is acquired by receiving the reflected light (S120).

At this time, the light entered through the distal end of an endoscope excites an observation target, and the light reflected from the observation target is transmitted to the first area camera 244 and the second area camera 254 through the relay lens 220.

The light source 400 may include two or more light sources having different wavelengths so as to image an observation target labeled with fluorescent samples having different wavelengths.

The first area camera 244 and the second area camera 254 may include a first area filter 242 and a second area filter 252, respectively, which may be realized by an LCTF as a local band-pass filter for passing the light of a specified spectral region.

Next, the auto-fluorescence portion included in the captured image is removed and is separated and outputted according to a predetermined wavelength band (step S130).

The fluorescence spectrum data obtained through the endoscope is outputted by being divided for each wavelength band through the division operation of the computing unit 300. The auto-fluorescence portion may be removed to finally acquire the desired image of a wavelength region to be obtained from the observation target.

The multi-wavelength endoscopic system 100 may store an auto-fluorescence spectrum and a single fluorescence spectrum result that represent light intensities according to wavelength bands of a pre-stored untreated tissue sample image and a tissue sample image obtained by single-processing using a fluorescent material.

At this time, it is possible to further store the normalized numerical value indicating the intensity of light according to the wavelength band calculated from the auto-fluorescence spectrum and the single fluorescence spectrum.

Then, the multi-wavelength endoscopic system 100 performs correction for removing the auto-fluorescence portion by attenuating the spectrum of the image data obtained by imaging the observation site labeled with a plurality of fluorescent materials by just as much as the normalized numerical value of the auto-fluorescence spectrum.

Then, the multi-wavelength endoscopic system 100 separates (unmix) the image spectrum result of the image data by the intensity of light corresponding to each wavelength band according to the normalized numerical value calculated from the single fluorescence spectrum, whereby the image of the observation site labeled with a plurality of fluorescent materials can be separated and displayed as a plurality of images so that only each fluorescent material appears.

That is, in the case where one marker is labeled with one fluorescence material, it is difficult to accurately determine a lesion. Therefore, in this embodiment, by labeling a lesion using a complex probe labeled with fluorescent materials having different wavelengths, it is possible to supplement mutually-different probes, thereby accurately imaging the lesion.

In addition, the computing unit 300 according to an embodiment of the present invention may perform a correction to remove the auto-fluorescence component from the multi-spectral image in order to reduce the probability of misdiagnosis when diagnosing a disease according to the imaging result. This makes it possible to display only a marker labeled with a fluorescent material.

FIGS. 6A to 6D are views showing a simulation apparatus for evaluating the performance of the multi-wavelength endoscopic system according to an embodiment of the present invention, and simulation results thereof.

Figure 6A:
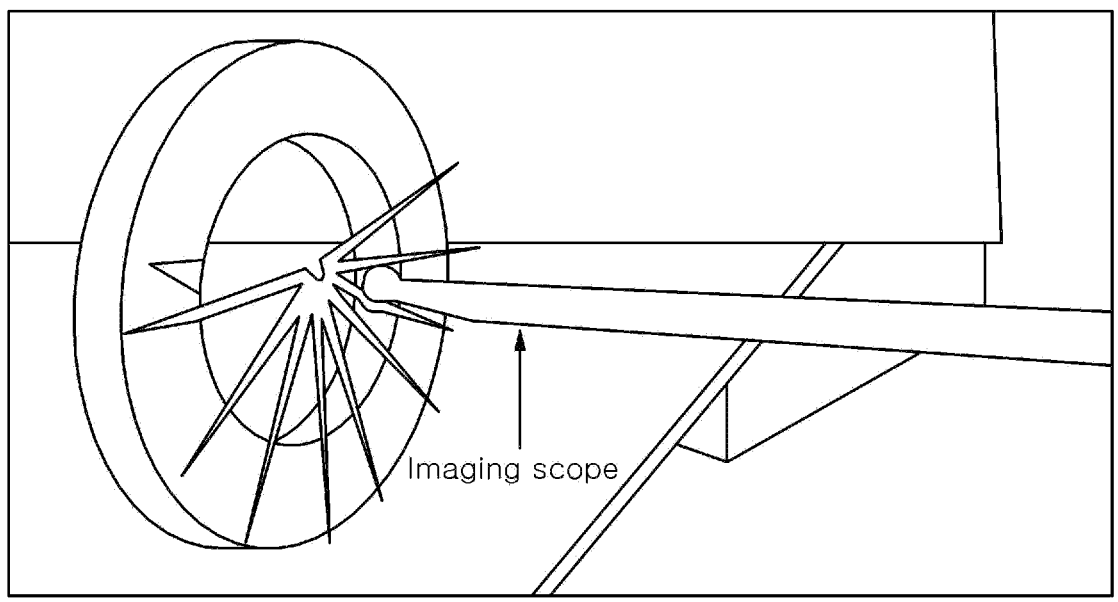
FIGS. 6A to 6D are views showing a simulation apparatus for evaluating the performance of the multi-wavelength endoscopic system according to an embodiment of the present invention and simulation results thereof.

Referring to FIG. 6A, polyethylene tubes (PE-10) having an inner diameter of 0.28 mm and a length of about 15 mm are prepared to evaluate the performance of the multi-wavelength endoscopic system according to an embodiment of the present invention. Fluorescent dyes having different colors are injected into the respective tubes.

One end of the tube is attached to a circular metal ring and the other end of the tube is narrowed toward the center at which endoscope observation is performed. The fluorescent dyes used have different colors of a visible light region band and contain wavelength regions close to each other.

Figure 6B:
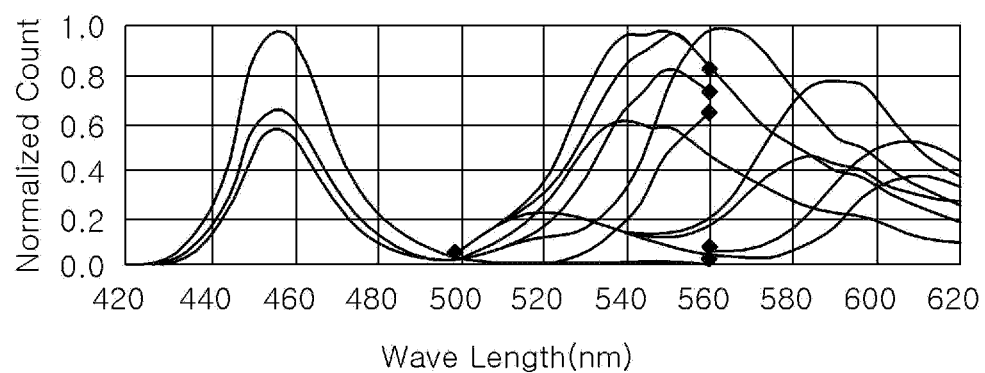
Figure 6C:
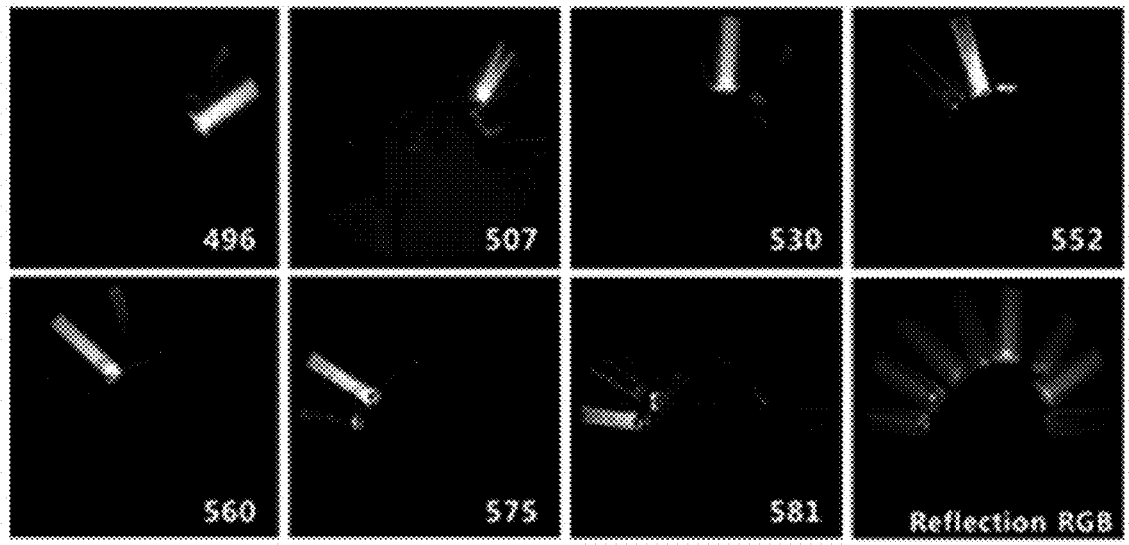

Referring to FIG. 6B, the tubes containing fluorescent dyes are respectively imaged to acquire image data. As shown in FIG. 6C, the spectra representing the intensities of light configured to the wavelength bands are obtained from the respective results of image data. This makes it possible to identify the separated regions for each wavelength of each dye.

In this case, the set wavelength range read in the multi-wavelength endoscopic system 100 according to the present embodiment may be 420 nm to 620 nm.

Figure 6D:
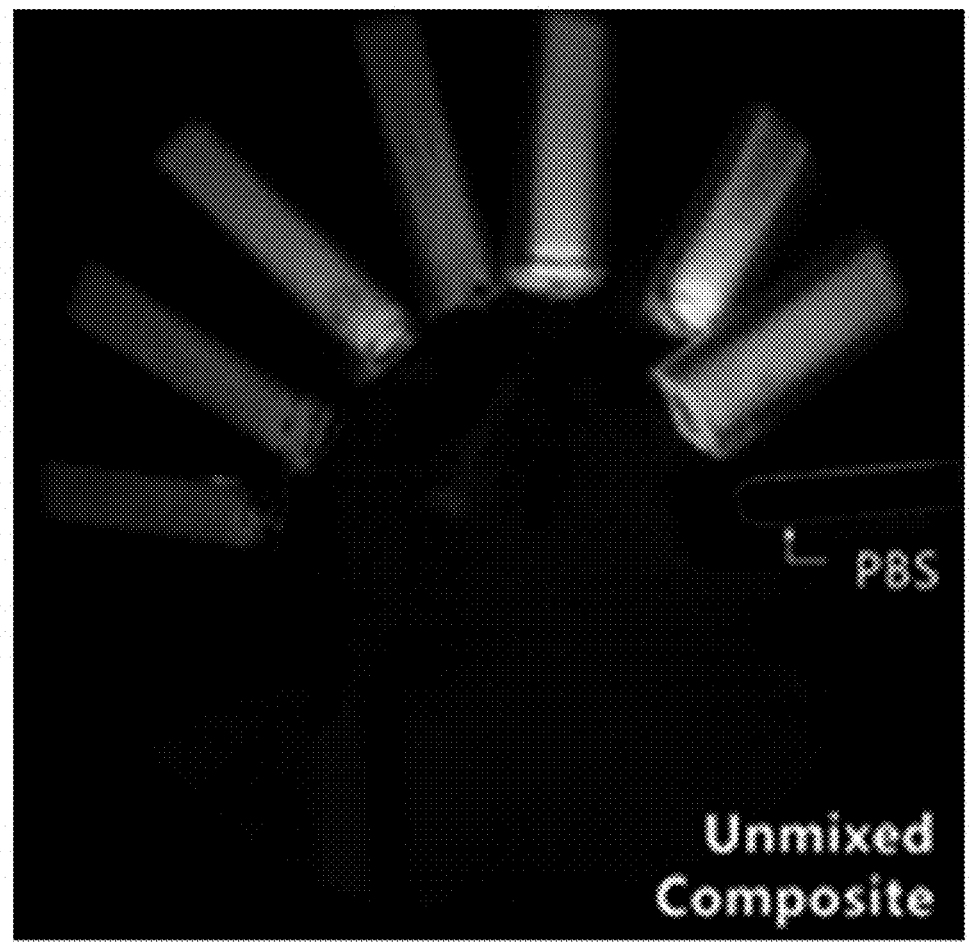

Referring to FIG. 6D, a complete image file is obtained by a decomposition process according to a single fluorescence spectrum result through the computing unit 300.

Figure 7:
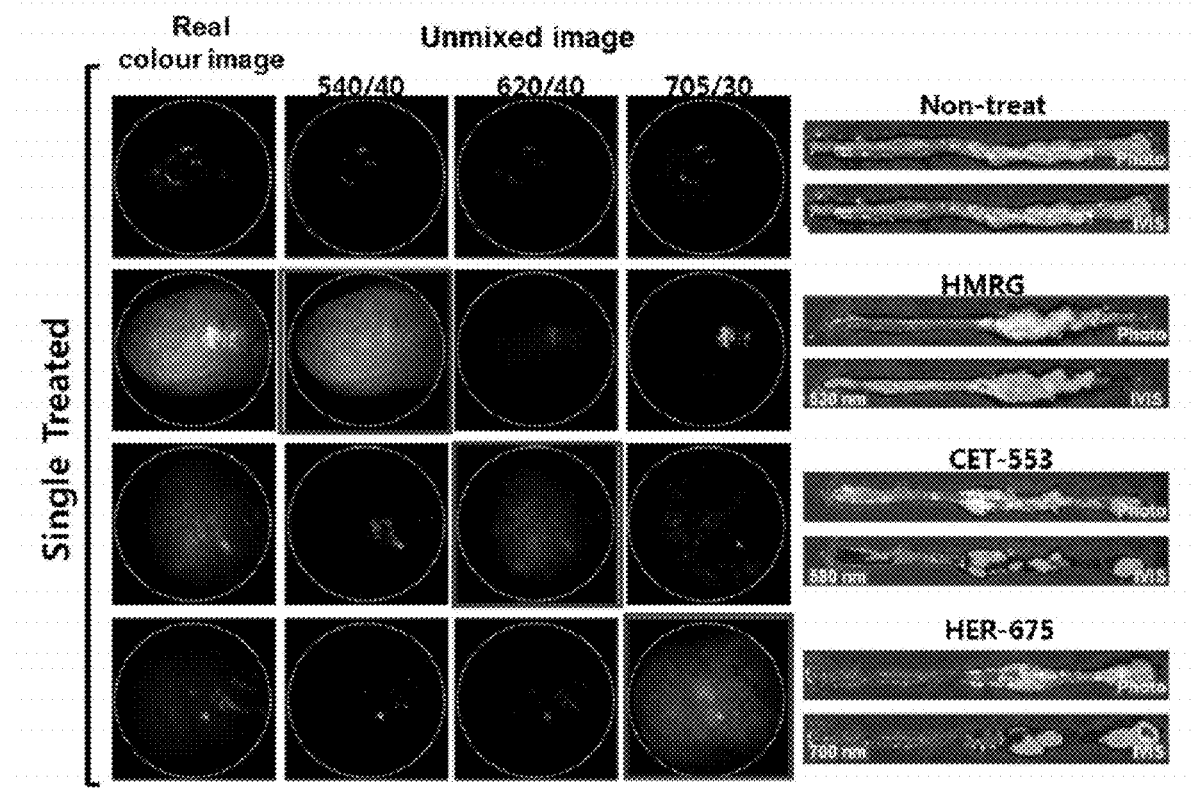
FIG. 7 is a diagram showing images obtained from an untreated tissue sample and a single fluorescence-treated tissue sample by the multi-wavelength endoscopic system according to an embodiment of the present invention.
Figure 8:
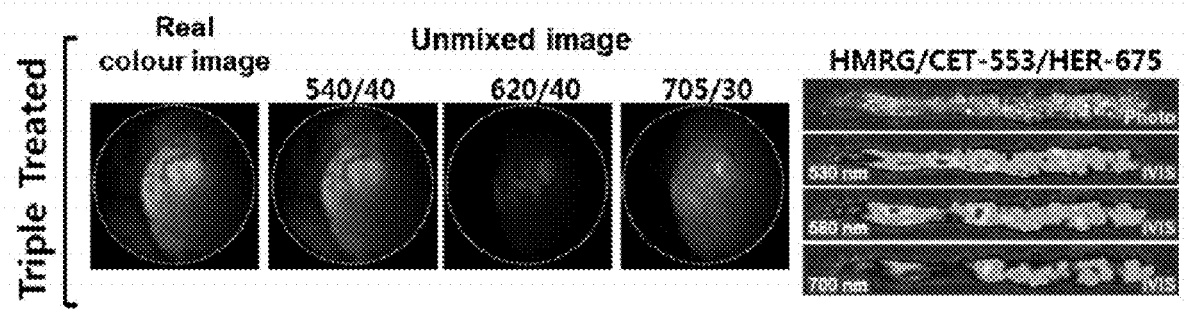
FIG. 8 is a view showing an endoscopic imaging result obtained by imaging a tissue sample treated with a plurality of fluorescent materials using the multi-wavelength endoscopic system according to an embodiment of the present invention.

FIG. 7 is a diagram showing images obtained from an untreated tissue sample and a single fluorescence-treated tissue sample by the multi-wavelength endoscopic system according to an embodiment of the present invention. FIG. 8 is a view showing an endoscopic imaging result obtained by imaging a tissue sample treated with a plurality of fluorescent materials using the multi-wavelength endoscopic system according to an embodiment of the present invention.

At this time, an active probe (HMRG) is injected by local application, and antibody probes (Cetuximab-Flamma553 and Herceptin-Flamma675) are intravenously injected. Then, colon tissue is extracted, and images corresponding to the respective wavelengths are acquired using the multi-wavelength endoscopic system 100.

Referring to FIG. 7, fluorescence images by auto-fluorescence can be observed in the non-treated colonic tissue of animals in which probes are not treated for control experiments.

A single probe-treated tissue sample is imaged at the observation site, and a single fluorescence spectrum result indicating the intensity of the light corresponding to the wavelength band is extracted from the captured image data.

Referring to FIG. 8, in this embodiment, a composite probe labeled with fluorescent materials having different wavelengths is used. In the image data obtained by imaging a tissue sample labeled with a complex probe, an image is separated and outputted so that only each fluorescent material is labeled according to a single fluorescence spectrum result. Therefore, it is possible to confirm that the imaging is performed so as to accurately diagnose a lesion by supplementing different probes.

Figure 9:
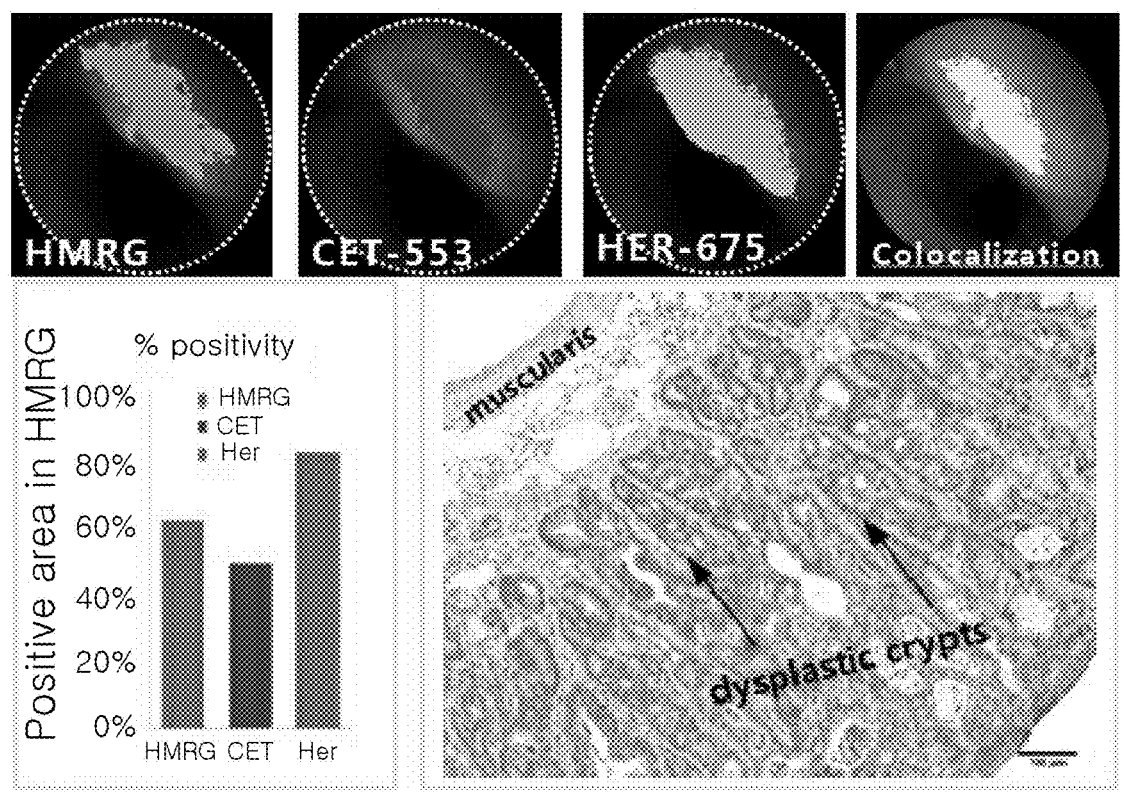
FIG. 9 is a view showing an endoscopic imaging result obtained by imaging a live colon cancer model mouse using the multi-wavelength endoscopic system according to an embodiment of the present invention.

FIG. 9 is a view showing an endoscopic imaging result obtained by imaging a live colon cancer model mouse using the multi-wavelength endoscopic system according to an embodiment of the present invention.

Active probes (HMRG) are injected into a colon cancer model mouse by local application, and antibody probes (Cetuximab-Flamma553 and Herceptin-Flamma675) are injected intravenously. Then, an image for each fluorescent material is acquired through colonoscopy using the multi-wavelength endoscopic system 100.

While it is difficult for the single probe to image and accurately determine the sections of cancer, the composite probe can supplement different probes and can image the sections of cancer.

Figure 10:
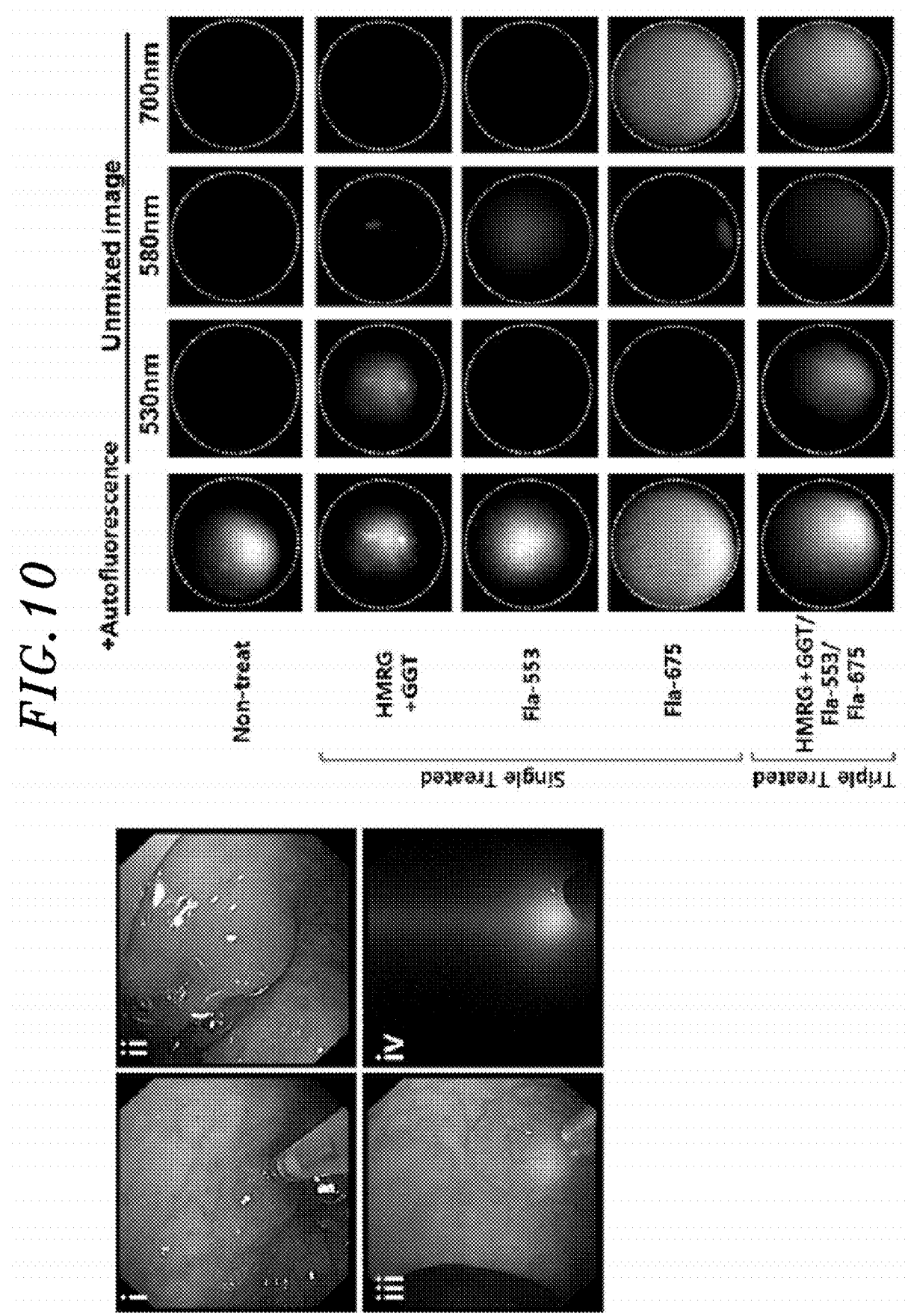
FIG. 10 is a view showing an endoscopic imaging result obtained by imaging a live colon cancer model pig using the multi-wavelength endoscopic system according to an embodiment of the present invention.

FIG. 10 is a view showing an endoscopic imaging result obtained by imaging a live colon cancer model pig using the multi-wavelength endoscopic system according to an embodiment of the present invention.

Active probes (HMRG) and antibody probes (Cetuximab-Flamma553 and Herceptin-Flamma675) are injected into a human-like pig. Then, an image for each wavelength is acquired through colonoscopy using the multi-wavelength endoscopic system 100.

A fluorescence image is not acquired when the probe is not processed for control experiments.

When each probe is single-treated with a fluorescent material, the signal is detected only at the spectrum wavelength of the fluorescence of each probe. Image data is separated from the triple-treated image data for three probes using the single fluorescence spectrum result so that only each fluorescent material is labeled.

Thus, by supplementing the different probes, it is possible to reduce false positive errors and to accurately image the sections of cancer.

The embodiments of the present invention described above are not implemented only by the apparatus and method, but may be implemented through a program for realizing the function corresponding to the configuration of the embodiment of the present invention or a recoding medium on which program is recorded.

While the disclosure has been shown and described with respect to the embodiments, it will be understood by those skilled in the art that various changes and modifications may be made without departing from the scope of the disclosure as defined in the following claims.

What is claimed is:

1. A multi-wavelength endoscopic system for imaging an observation site labeled with a plurality of fluorescent materials having different colors, comprising:
    an imaging unit configured to acquire image data by polarizing incident light reflected from the observation site in a first direction and a second direction perpendicular to the first direction, dividing a spectrum region of the incident light polarized in the first direction and the second direction into a plurality of spectrum channels and measuring an intensity of light for each of the spectrum channels; and
    a computing unit configured to store a single fluorescence spectrum extracted from sample image data obtained by single-treating the observation site with each of the fluorescent materials and configured to separate and output the image data obtained in the imaging unit using the single fluorescence spectrum so that each of the fluorescent materials is displayed separately,
    wherein the computing unit is configured to store an untreated fluorescence spectrum extracted from untreated image data obtained by imaging the observation site not labeled with the fluorescent materials, and
    wherein the computing unit is configured to perform a correction to remove an auto-fluorescence component contained in the image data obtained in the imaging unit using the untreated fluorescence spectrum.

2. The system of claim 1, wherein the imaging unit includes:
- a beam splitter configured to polarize the incident light in the first direction and the second direction perpendicular to the first direction;
- a first area filter positioned in a path of a light beam split in the first direction and configured to pass a light beam falling within a predetermined spectral range;
- a second area filter positioned in a path of a light beam split in the second direction and configured to pass a light beam falling within a predetermined spectral range;
- a first area camera configured to measure an intensity of the light beam passing through the first area filter; and
- a second area camera configured to measure an intensity of the light beam passing through the second area filter.

3. A multi-wavelength endoscopic system for imaging an observation site labeled with a plurality of fluorescent materials having different colors, comprising:
- a beam splitter configured to polarize incident light reflected from the observation site in a first direction and a second direction perpendicular to the first direction;
- a first area filter positioned in a path of a light beam split in the first direction and configured to pass a light beam falling within a predetermined spectral range;
- a second area filter positioned in a path of a light beam split in the second direction and configured to pass a light beam falling within a predetermined spectral range;
- a first area camera configured to measure an intensity of the light beam passing through the first area filter;
- a second area camera configured to measure an intensity of the light beam passing through the second area filter; and
- a computing unit configured to separate and output the image data obtained using the intensity of the light beam passing through the first area filter and the intensity of the light beam passing through the second area filter so that each of the fluorescent materials is displayed separately,
- wherein the computing unit is configured to store an untreated fluorescence spectrum extracted from untreated image data obtained by imaging the observation site not labeled with the fluorescent materials, and
- wherein the computing unit is configured to perform a correction to remove an auto-fluorescence component contained in the image data using the untreated fluorescence spectrum.

4. The system of claim 3, wherein the computing unit is configured to store a single fluorescence spectrum extracted from sample image data obtained by single-treating the observation site with each of the fluorescent materials and is configured to separate the image data using the single fluorescence spectrum so that each of the fluorescent materials is displayed separately.

5. An image processing method for processing an image using a multi-wavelength endoscopic system having an imaging unit and a computing unit, comprising:
- irradiating light on an observation site labeled with a plurality of fluorescent materials having different colors using the imaging unit;
- acquiring image data by receiving a light reflected from the observation site using the imaging unit;
- separating the image data so that only one of the fluorescent materials is displayed using the computing unit; and
- outputting the separated image data according to a wavelength band using the computing unit; and
- extracting an untreated fluorescence spectrum from untreated image data obtained by imaging the observation site not labeled with the fluorescent materials, and performing a correction to remove an auto-fluorescence component contained in the image data using the untreated fluorescence spectrum using the computing unit.

6. The method of claim 5, wherein said separating the image data so that only one of the fluorescent materials is displayed using the computing unit further comprises:
- extracting a single fluorescence spectrum from sample image data obtained by single-treating the observation site with each of the fluorescent materials.

7. The method of claim 6, wherein said separating the image data so that only one of the fluorescent materials is displayed using the computing unit further comprises:
- the image data is separated using the single fluorescence spectrum so that each of the fluorescent materials is displayed separately.

* * * * *